United States Patent

Block et al.

4,022,757

May 10, 1977

[54] DICARBAMIC ACID DIESTERS CONTAINING PHOSPHORUS

[75] Inventors: Hans-Dieter Block; Udo-Winfried Hendricks, both of Cologne; Klaus Walz, Bergisch-Neukirchen, all of Germany

[73] Assignee: Bayer Aktiengesellschaft, Leverkusen, Germany

[22] Filed: Jan. 17, 1975

[21] Appl. No.: 542,049

[30] Foreign Application Priority Data

Jan. 17, 1974 Germany .......................... 2402174

[52] U.S. Cl. ........................... 260/932; 106/15 FP; 260/927 R; 428/276; 428/277
[51] Int. Cl.² ........................................... C07F 9/28
[58] Field of Search ................ 260/932, 927 R, 938

[56] References Cited

UNITED STATES PATENTS

| 2,989,562 | 6/1961 | Swern ................... 260/932 X |
| 3,679,778 | 7/1972 | Nachbur et al. ............. 260/932 |
| 3,763,283 | 10/1973 | Curgan ................... 260/938 |
| 3,835,204 | 9/1974 | Weil ..................... 260/938 |
| 3,899,549 | 8/1975 | Petersen et al. ............ 260/932 |
| 3,906,063 | 9/1975 | Hendricks et al. ........... 260/932 |

*Primary Examiner*—Richard L. Raymond
*Attorney, Agent, or Firm*—Plumley and Tyner

[57] ABSTRACT

Dicarbamic acid diesters of the formula

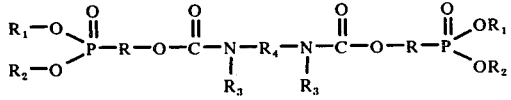

in which R represents $C_1 - C_4$-alkylene which is optionally substituted by one or more halogen atoms, and $R_1$ and $R_2$ independently of one another represent $C_1 - C_4$-alkyl which is optionally substituted by halogen atoms or together with the oxygen atoms and the phosphorus atom form a 5-membered to 7-membered heterocyclic structure, $R_3$ is hydrogen, hydroxymethyl or $C_1 - C_4$-alkoxymethyl and $R_4$ represents a divalent radical, with at least 2 carbon atoms, which is free from hydroxyl groups, and of which the two bonds must start from different carbon atoms, and wherein the phosphorus content of the diester is more than 5 % by weight, are suitable as flameproofing agents for textile materials, paper and plastics.

3 Claims, No Drawings

DICARBAMIC ACID DIESTERS CONTAINING PHOSPHORUS

The invention relates to new dicarbamic acid diesters containing phosphorus, of the formula

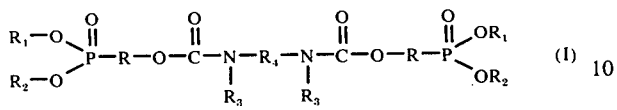
(I)

in which
- R represents a straight-chain or branched $C_1$–$C_4$-alkylene radical which is optionally substituted by one or more halogen atoms, preferably chlorine atoms,
- $R_1$ and $R_2$ independently of one another represent a $C_1$–$C_4$-alkyl radical which is optionally substituted by halogen atoms, preferably chlorine or bromine atoms, or together with the oxygen atoms and the phosphorus atom form a 5-membered to 7-membered heterocyclic structure,
- $R_3$ is hydrogen, a hydroxymethyl or a $C_1$–$C_4$-alkoxymethyl group and
- $R_4$ represents a divalent radical, with at least 2 carbon atoms, which is free from hydroxyl groups, and of which the two bonds must start from different carbon atoms, and wherein the phosphorus content of the diester is more than 5% by weight, processes for their preparation and their use as flameproofing agents for textile materials, paper and plastics.

The radicals $R_1$ and $R_2$ together with the oxygen atoms and the phosphorus atom in particular form a ring of the 1,3-dioxa-2-phospholane, 1,3-dioxa-2-phosphirane or 1,3-dioxa-2-phospha-cycloheptane series.

$R_4$ preferably represents a divalent aliphatic, cycloaliphatic, aromatic or araliphatic radical which can be interrupted by hetero-atoms or groups of atoms containing the latter, or by cyclic radicals. Compounds of the formula I in which R represents methylene are also preferred. For example, $R_4$ represents a straight-chain or branched, optionally halogen-substituted, $C_2$–$C_9$-alkylene radical, or a phenylene, cyclohexylene, toluylene, xylylene or diphenylenemethane radical which is optionally substituted by $C_1$–$C_4$-alkyl, halogen or a $C_1$–$C_4$-alkoxy-carbonyl radical.

Preferred diesters I are those in which R represents the methylene, ethylene-(1,2), propylene-(1,3) or propylene-(1,2) radical, $R_1$ and $R_2$ represent methyl and-/or ethyl and $R_4$ represents $C_2$–$C_6$-alkylene, cyclohexylene, phenylene or toluylene radicals. In diesters I which should be singled out particularly, R denotes the ethylene-(1,2) or propylene-(1,3) radical, $R_1$ and $R_2$ denote methyl and/or ethyl, $R_3$ denotes hydrogen and/or hydroxymethyl and/or methoxymethyl and $R_4$ denotes cyclohexylene, phenylene or toluylene radicals.

The compounds according to the invention, of the formula I, can be prepared according to various processes.

Process A

This process starts from hydroxyalkanephosphonic acid esters of the formula

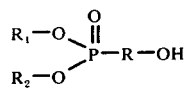
II in which R, $R_1$ and $R_2$ have the meaning indicated under formula I.

These compounds of the formula II, which are obtainable according to processes which are in themselves known, are reacted, again in a manner which is in itself customary, with compounds containing at least 2 isocyanate groups, of the formula $$O=C=N-R_4-N=C=O$$ III in which $R_4$ has the meaning indicated under the formula I and are optionally subsequently methylolated with formaldehyde in the usual manner, and the resulting methylol compounds are optionally etherified with $C_1$–$C_4$-alcohols in a known manner.

The process is carried out, for example, by reacting the compounds of the formula II, optionally in the presence of catalysts, such as, for example, tert. amines or tin-(II) octoate, and optionally in an inert solvent, for example benzene, toluene, dioxane, tetrahydrofurane or acetonitrile, at temperatures of 0°–150° and preferably 40°–110°, with the isocyanates of the formula III, employing at least 2 mols of the compound of the formula II per 1 mol of the compound containing isocyanate groups, of the formula III. The resulting reaction products are optionally converted to the N-hydroxymethyl compounds in a known manner with aqueous formaldehyde solution or formaldehyde donor compounds, such as paraformaldehyde or trioxane, with addition of alkaline catalysts, for example sodium hydroxide, potassium hydroxide, sodium carbonate or potassium carbonate.

The following may be mentioned as examples of hydroxyalkanephosphonic acid esters of the formula II: hydroxymethanephosphonic acid dimethyl ester, hydroxymethanephosphonic acid diethyl ester, 2-hydroxyethanephosphonic acid dimethyl ester, 2-hydroxyethanephosphonic acid diethyl ester, 2-hydroxyethanephosphonic acid di-n-propyl ester, 2-hydroxyethanephosphonic acid di-n-butyl ester, 2-hydroxyethanephosphonic acid di-isobutyl ester, 2-hydroxyethanephosphonic acid di-(2-chloroethyl) ester, 2-hydroxyethanephosphonic acid diallyl ester, 2-hydroxyethanephosphonic acid bis-(2,3-di-bromopropyl) ester, 1-hydroxyethanephosphonic acid dimethyl ester, 1-hydroxy-2,2,2-trichloroethanephosphonic acid dimethyl ester, 2-hydroxypropane-2-phosphonic acid dimethyl ester, 2-hydroxypropanephosphonic acid dimethyl ester, 3-hydroxypropane-phosphonic acid dimethyl ester, 3-hydroxypropanephosphonic acid diethyl ester, 2-hydroxy-3-bromopropanephosphonic acid dimethyl ester and 1-hydroxy-2,3-dibromopropanephosphonic acid dimethyl ester.

The following may be mentioned as examples of the compounds III: ethylenediisocyanate, butylenediisocyanate, hexamethylenediisocyanate, 2,2,4-trimethyl-hexamethylenediisocyanate, butylene glycol 1,4-bis-(isocyanatomethyl) ether, ethylene glycol bis-α-isocyanatoethyl ether, cyclohexanediisocyanate, isophoronediisocyanate, 4,4'-diisocyanato-dicyclohexylmethane, xylylenediisocyanate, phenylenediisocyanate, toluylenediisocyanate, mono-, di-, tri- and tetra-bromophenylenediisocyante, 5-chloro-toluylene-2,4-diisocyanate, 4,4'-diisocyanato-diphenylmethane, 3,3', 5,5'-tetrabromo-4,4'-diisocyanato-diphenylmethane, 4,4'-diisocyanato-diphenyl ether, 1,3-bis-(4-methyl-3-isocyanatophenyl)uretdione and 1,3,5-tris-(4-methyl-3-isocyanatophenyl)-isocyanurate.

Reaction products of 1 mol of compounds which contain at least 2 reactive hydrogen atoms with at least 2 mols of one of the abovementioned diisocyanates can also be used as further isocyanates of the formula III. Suitable compounds can be prepared, for example, by reaction of tetramethylene-, hexamethylene-, phenylene- or toluylene-diisocyanate with polyols or polyamines, such as ethylene glycol, propylene glycol, butylene glycol, butenediol, 2-chloropropanediol-1,3, 2,3-dibromobutanediol-1,4 2-methylenepropanediol, 2-bromo-2-bromomethyl-propanediol, dibromoneopentyl glycol, methanephosphonic acid bis-hydroxyethyl ester, trishydroxyethyl phosphate, diethylene glycol, bis-hydroxyethyl sulphide, thioethylene glycol, ethylenediamine, butylenediamine, diaminocyclohexane or N,N-bis-hydroxyethylamino-methane-phosphonic acid diethyl ester.

In a preferred embodiment, hydroxymethanephosphonic acid dialkyl esters or hydroxyethanephosphonic acid dialkyl esters are reacted with $C_2$–$C_6$-alkylenediisocyanate and/or cyclohexylenediisocyanate, phenylenediisocyanate or toluylenediisocyanate.

Process B

This starts from dicarbamic acid esters of the formula

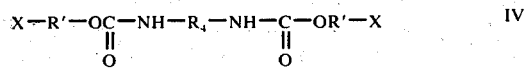

in which
X represents a chlorine or bromine atom and
R' represents a $C_2$–$C_4$-alkylene radical and
$R_4$ has the meaning indicated under formula I.
These compounds of the formula IV are reacted with phosphorous acid trialkyl esters of the formula

in which
$R_5$, $R_6$ and $R_7$ independently of one another represent a $C_1$–$C_4$-alkyl radical or
$R_5$ and $R_6$ together with the oxygen atoms and the phosphorus atom form a 5-membered to 7-membered heterocyclic structure at 100°–200°, preferably 130°–180°, optionally in the presence of diluents which are inert under the reaction conditions, and are optionally subsequently methylolated with formaldehyde in the usual manner, and the resulting methylol compounds are optionally etherified with $C_1$–$C_4$-alcohols in a known manner.

The following may be mentioned as examples of dicarbamic acid esters of the formula IV: N,N'-ethylene-bis-(carbamic acid chloroethyl ester), N,N'-propylene-bis-(carbamic acid chloroethyl ester), N,N'-butylene-bis-(carbamic acid chloroethyl ester), N,N'-butylene-bis-(carbamic acid 3-chloropropyl ester), N,N'-butylene-bis-(carbamic acid bromoethyl ester), N,N'-hexamethylene-bis-(carbamic acid 2-chloroethyl ester) and N,N'-hexamethylene-bis-(carbamic acid 2-bromoethyl ester).

Furthermore it is possible to use compounds which are obtained by reaction of the isocyanates mentioned under process A with chloroethanol, bromoethanol, 2-chloropropanol, 3-chloropropanol, 3bromopropanol or chlorinated or brominated butanols.

The following may be mentioned as examples of phosphorous acid trialkyl esters of the formula V: trimethyl phosphite, triethyl phosphite, tri-n-propyl phosphite, triisopropyl phosphite, tri-isobutyl phosphite, dimethylethyl phosphite, 2-methoxy-1,3-dioxa-phospholane and 2-ethoxy-4-methyl-1,3-dioxa-phospholane.

In a preferred embodiment, N,N'-$C_2$-$C_6$-alkylene-bis-(carbamic acid 2-chloroethyl esters) or the corresponding 2-bromoethyl esters are reacted with trimethyl phosphite and/or triethyl phosphite.

Process C

This starts from dicarbamic acid esters of the formula

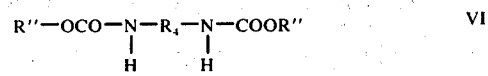

in which
$R^4$ has the meaning indicated under formula I and
R" represents a $C_2$–$C_4$-alkenyl radical;
these compounds of the formula VI are reacted with phosphorous acid dialkyl esters of the formula

in which $R_5$ and $R_6$ have the meaning indicated under formula V in the presence of radical-forming catalysts and subsequently optionally methylolated with formaldehyde, and the methylol compounds are optionally etherified with $C_1$–$C_4$-alcohols.

The reaction of the compounds of the formula VI with the phosphorous acid dialkyl esters of the formula VII is preferably carried out using excess phosphorous acid dialkyl ester at temperatures of 70°–250° C, preferably 100°–140° C. As radical-forming catalysts it is possible to use organic peroxides, for example dibenzoyl peroxide, di-tert.-butyl peroxide or dicumyl peroxide, or azo compounds, such as azoisobutyric acid dinitrile. The catalysts are employed in amounts of about 0.1–30 mol % based on the weight of the compounds of the formula VI.

In a preferred embodiment of process C, N,N'-$C_2$-$C_6$-alkylene-bis-(carbamic acid allyl esters) or N,N'-$C_2$-$C_6$-alkylene-bis-(carbamic acid methylallyl esters) are reacted with dimethyl phosphite and/or diethyl phosphite and the resulting dicarbamic acid esters are optionally subsequently methylolated with formaldehyde and the methylol compounds are optionally etherified with methanol.

Process D

This starts from chloroformic acid esters of the formula

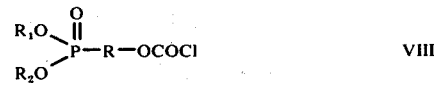

in which

R, $R_1$ and $R_2$ have the meaning indicated under the formula I;

these compounds are reacted with amines of the formula $$NH_2-R_4-NH_2 \qquad IX$$

in which $R_4$ has the meaning indicated under formula I, optionally in the presence of acid acceptors, such as hydroxides, oxides, carbonates or bicarbonates of alkali metals or alkaline earth metals, or tertiary amines, such as triethylamine or pyridine. The resulting dicarbamic acid esters are optionally converted into the methylol compounds under the conditions described in process A and optionally subsequently converted into the methylol ethers. The reaction can be carried out in the aqueous phase or in organic solvents, such as methanol, ethanol, acetone, acetonitrile, dimethylformamide, pyrrolidine or optionally halogenated hydrocarbons, at −10° to +50°.

In a preferred embodiment, the chloroformic acid esters of hydroxymethanephosphonic acid dimethyl ester or diethyl ester or 2-hydroxyethane dimethyl ester or diethyl ester are reacted with ethylenediamine, propylenediamine, butylenediamine or hexamethylenediamine or with 1,4-diaminocyclohexane and the resulting dicarbamic acid esters are optionally methylolated with formaldehyde.

The majority of the compounds according to the invention, of the formula I, are highly viscous, colourless or slightly coloured liquids or crystalline products. They are outstandingly suitable for the flameproof finishing of fibre materials consisting of natural or synthetic fibres, and of plastics. Using the compounds according to the invention, an excellent wash-resistant flameproofing finish is achieved on textiles of fibre materials containing cellulose, such as cotton, linen, viscose or rayon and polyester-cotton mixtures.

The dicarbamic acid diesters according to the invention, of the formula I, are employed in an amount of about 8 to 60, preferably 10 to 40, % by weight based on the fibre material when used as flameproofing agents for textile materials.

For finishing, the textile materials are impregnated with solutions which contain, per liter, about 100 to 400 g of the compounds according to the invention, of the formula I, and optionally further finishing agents, such as creaseproofing agents, softeners, hydrophobic agents and oleophobic agents and acid or latent acid condensation catalysts. The solvent used is preferably water, optionally mixed with water-miscible organic solvents and optionally using small amounts of emulsifiers. The fibre materials are impregnated with the finishing liquors in a known manner, for example by dipping, padding or spraying, squeezed off to a weight increase of about 80–150% and subsequently dried and thermofixed at 100°–200° C, preferably 140°–180° C.

The parts indicated in the examples which follow are parts by weight, unless stated otherwise.

EXAMPLE 1

924 parts of 2-hydroxyethanephosphonic acid dimethyl ester are mixed with 2 parts of triethylamine, the mixture is heated to 70°–80° C and 504 parts of hexamethylenediisocyanate are added slowly, whilst stirring. After completion of the addition, the reaction mixture is stirred for a further 5 hours at 80° C. 1,420 parts of a colourless viscous product which corresponds to the formula $$\begin{array}{c} CH_3O \\ \phantom{CH_3O}\diagdown \\ CH_3O \phantom{\diagup} \end{array} \!\! \overset{O}{\underset{}{P}} \!\!-\!CH_2CH_2O\overset{O}{\underset{}{C}}\!-\!NH\!-\!(CH_2)_6\!- $$

$$-NH-\overset{O}{\underset{}{C}}-OCH_2CH_2\overset{O}{\underset{}{P}}\!\!\diagup\!\!\overset{OCH_3}{\diagdown OCH_3}$$

are obtained. On being left to stand, the product solidifies to colourless crystals of melting point 56°–58°.

$C_{16}H_{34}N_2O_{10}P_2$ (476); Calculated: C, 40.3; H, 7.1; N, 5.88; P, 13.0. Found: C, 40.3; H, 7.4; N, 6.0; P, 13.3.

EXAMPLE 2

141 parts of the product described in Example 1 are mixed with 50 parts of water and brought to pH 8 with 3 parts of concentrated sodium hydroxide solution. The mixture is heated to 50°–60° and 48 parts of 37% strength formaldehyde solution are then added. The mixture is stirred for a further ½ hour at 50°–60° and is then freed from water in vacuo at down to 2 mm Hg. 156 parts of the compound of the formula $$\begin{array}{c}CH_3O\\ \diagdown\\ CH_3O\diagup\end{array}\!\!\overset{O}{\underset{}{P}}\!-\!CH_2CH_2O\overset{O}{\underset{\parallel}{C}}\!-\!\underset{CH_2OH}{N}\!-\!(CH_2)_6\!-\!\underset{CH_2OH}{N}\!-\!\overset{O}{\underset{}{C}}\!-\!OCH_2CH_2\overset{O}{\underset{}{P}}\!\!\diagup\!\!\overset{OCH_3}{\diagdown OCH_3}$$

are obtained as a colourless, highly viscous liquid. $n_D^{20}$ =1.474.

$C_{18}H_{38}N_2O_{12}P_2$ (540); Calculated: C, 40.0; H, 7.04; N, 5.19; P 11.47. Found: C, 39.2; H, 7.2; N, 5.1; P, 12.0.

EXAMPLE 3

308 parts of 2-hydroxyethanephosphonic acid dimethyl ester and 1 part of triethylamine are dissolved in 500 ml of acetonitrile and 160 parts of phenylene-1,4-diisocyanate are added in portions over the course of ½ hour at 60°–70° C. The mixture is stirred for a further 3 hours at 70° and the product which crystallises out is filtered off after cooling. The product is washed with cold acetonitrile and dried.

Yield: 285 parts. Melting point 175°–177° C.

$$\begin{array}{c}CH_3O\\ \diagdown\\ CH_3O\diagup\end{array}\!\!\overset{O}{\underset{}{P}}\!-\!CH_2CH_2O\overset{O}{\underset{}{C}}\!-\!NH\!-\!\!\left\langle\!\!\!\begin{array}{c}\\ \\ \end{array}\!\!\!\right\rangle\!\!-$$

$$-NH-\overset{O}{\underset{}{C}}-O-CH_2CH_2-\overset{O}{\underset{}{P}}\!\!\diagup\!\!\overset{OCH_3}{\diagdown OCH_3}$$

$C_{16}H_{26}N_2O_{10}P_2$ (468); Calculated: C, 41.0; H, 5.55; N, 5.97; P, 13.25. Found: C, 41.5; H, 5.7; N, 6.0; P, 13.1.

EXAMPLE 4

154 parts of 2-hydroxyethanephosphonic acid dimethyl ester are mixed with 90 parts of acetonitrile and 0.5 part of triethylamine and 87 parts of toluene-2,4-diisocyanate are then added slowly at 60°–70°. The mixture is stirred for a further 3 hours at 70° and the solvent is distilled off in vacuo. The resulting product is diluted with 100 parts of water and 4 parts of concentrated sodium hydroxide solution and 69 parts of 37% strength aqueous formaldehyde are added. The mixture is heated to 50°–60° for ½ hour, after which the water is distilled off at 60°–70° under a vacuum of down to 2 mm Hg.

289 parts of the compound

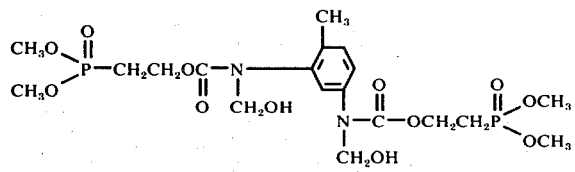

are obtained as a colourless, water-soluble resin. $C_{19}H_{32}N_2O_{12}P_2$ (542); Calculated: C, 42.0; H, 5.9; N, 5.16; P 11.43. Found: C, 41.0; H, 6.0; N, 5.2; P 11.5.

EXAMPLE 5

27 parts of ethylenediamine are dissolved in 500 parts of ethanol and 84 parts of finely ground sodium bicarbonate are then added. 196 parts of the chloroformic acid ester of 2-hydroxyethanephosphonic acid dimethyl ester are slowly added dropwise to the suspension, cooled to 0°–10°, whilst stirring. After completion of the addition, the temperature is allowed to rise to 20°–25° and the mixture is stirred for a further 15 hours at this temperature. The sodium chloride formed is filtered off and the filtrate is concentrated in vacuo. 192 parts of the compound

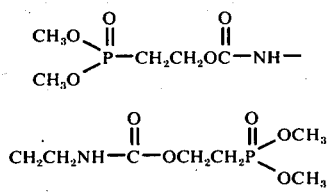

are obtained as a highly viscous, colourless liquid. $C_{12}H_{26}N_2O_{10}P_2$ (420) — $n_D^{60} = 1.4647$; Calculated: C, 34.35; H, 6.2; P, 14.65. Found: C, 34.9; H, 6.5; P, 14.5.

EXAMPLE 6

154 parts of 2-hydroxyethanoephosphonic acid dimethyl ester were dissolved in 250 parts of toluene and 1 part of triethylamine was added. A solution of 83 parts of cyclohexane-1,4-diisocyanate in 80 parts of toluene was added dropwise at 50°–60°. The reaction mixture was then heated to 110 –110° and kept at this temperature for 3 hours. After distilling off the solvent in a water-pump vacuum, 234 parts of a viscous residue remained; this residue crystallised slowly and was recrystallised from methanol.

Melting point: 161°–165°.

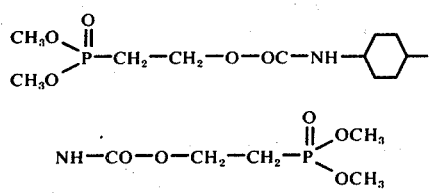

$C_{16}H_{32}N_2O_{10}P_2$ (474); Calculated: C, 40.5%; H, 6.74%; N, 5.92%; P, 13.09%. Found: C, 40.3%; H, 6.9%; N, 6.1; P, 13.2%.

EXAMPLE 7

168 parts of hydroxymethanephosphonic acid diethyl ester were dissolved in 200 parts of toluene and 0.3 part of tin-(II) octoate was added. 81 parts of hexamethylenediisocyanate were added dropwise at 60°–70°; the reaction mixture was then boiled for 3 hours at the reflux temperature. After evaporation in a water pump vacuum, 249 parts of a colourless, viscous residue of refraction index $n_D^{20} = 1.4698$ remained.

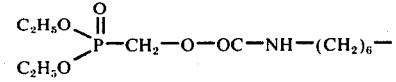

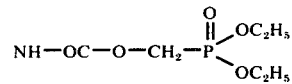

$C_{18}H_{38}N_2O_{10}P_2$ (504); Calculated: N, 5.56%; P, 12.3%. Found: N, 5.62%; P, 12.8%.

EXAMPLE 8

140 parts of hydroxymethanephosphonic acid dimethyl ester were dissolved in 200 parts of acetonitrile and 0.3 part of tin-(II) octate was added. 84 parts of hexamethylenediisocyanate were added dropwise at 70°–80°. The reaction mixture was then stirred for 3 hours at the reflux temperature. After distilling off the solvent in a water pump vacuum, 223 parts of a colourless, viscous residue of refraction index $n_D^{20}$ 1.4749 remained.

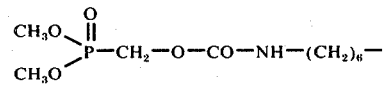

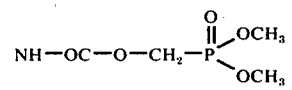

$C_{14}H_{30}N_2O_{10}P_2$ (448); Calculated: N, 6.25%; P, 13.84%. Found: N, 61.%; P, 14.00%.

EXAMPLE 9

167 parts of a 37% strength formaldehyde solution were adjusted to pH 8–8.5 with 20% strength sodium hydroxide solution. 418 parts of the phosphonic acid ester described in the preceding example were added dropwise to this solution at 40°–45°, and at the same time the pH value of the reaction mixture is kept at 8–8.5 by occasional addition of 20% strength sodium hydroxide solution. This mixture was then stirred for a further 2 hours at 40°–45°.

The water was distilled from a part of the reaction mixture in vacuo. A colourless viscous residue of refractive index $n_D^{20}$ 1.4589 remained.

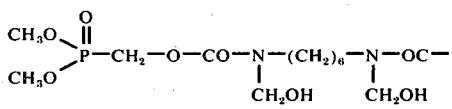

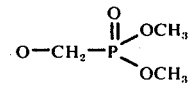

$C_{16}H_{34}N_2O_{12}P_2$ (568); Calculated: N, 4.92%, 10.92%. Found: N, 4.9%; P, 11.6%.

EXAMPLE 10

A cotton decorative fabric is impregnated with an aqueous liquor which contains, per liter, 300 g of the product described in Example 2, 150 g of hexamethylolmelamine 20 g of phosphoric acid and 1 g of a reaction product of 1 mol of nonylphenol with 10 mols of ethylene oxide. The impregnated fabric is squeezed off to a weight increase of 90–100%, dried for 10 minutes at 100° and condensed for 5 minutes at 165° C. The fabric is then washed with a dilute sodium carbonate solution at 40° C, and dried.

To test its flame-retarding properties, the fabric finished in this way was subjected to the vertical test according to DIN 53,906. The results of the test are summarised in the table which follows:

|   |   | Burning length | |
|---|---|---|---|
|   |   | Warp | Weft |
| A | untreated | burnt away | |
| B | finished according to Example | 7.4 cm | 6.9 cm |
| C | B after 10 machine washes at the boil | 7.2 cm | 10.9 cm |

We claim:

1. Dicarbamic diesters of the formula

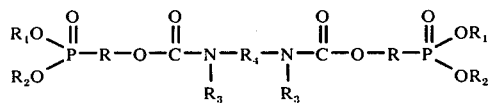

wherein

R is straight-chain or branched $C_1$–$C_4$ alkylene unsubstituted or substituted with at least one halogen atom;

$R_1$ and $R_2$ independently of one another are $C_1$–$C_4$ alkyl unsubstituted or substituted with halogen or together with the oxygen atoms and phosphorus atom form a 5- to 7-membered heterocyclic structure;

$R_3$ is hydrogen, hydroxymethyl, or $C_1$–$C_4$ alkoxymethyl;

$R_4$ is phenylene; cyclohexylene; toluylene; xylylene; diphenylenemethane which is unsubstituted or substituted with $C_1$–$C_4$ alkyl, halogen, or $C_1$–$C_4$ -alkoxycarbonyl; of which the two bonds must start from different carbon atoms and wherein the phosphorus content of the diester is more than 5% by weight.

2. Dicarbamic acid diesters according to claim 1 wherein

R is ethylene-(1,2) or propylene-(1,3);

$R_1$ and $R_2$ independently of one another are methyl or ethyl;

$R_3$ is hydrogen, hydroxymethyl or methoxymethyl; and $R_4$ is cyclohexylene, phenylene or toluylene.

3. Dicarbamic acid diester according to claim 1 of the formula

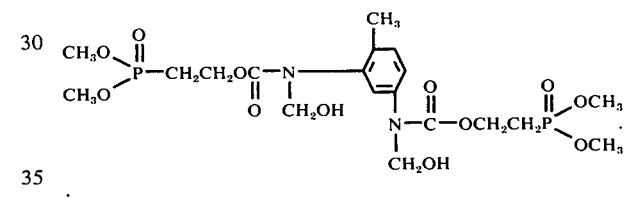

* * * * *